US009351780B2

(12) United States Patent
Arthur et al.

(10) Patent No.: US 9,351,780 B2
(45) Date of Patent: May 31, 2016

(54) SURGICAL DEVICE WITH RATCHET MECHANISM FOR PERFORMING A SURGICAL PROCEDURE AND METHOD

(71) Applicant: KYPHON SARL, Neuchatel (CH)

(72) Inventors: Amy L. Arthur, Mountain View, CA (US); Mojan Goshayeshgar, Atherton, CA (US)

(73) Assignee: KYPHON SÀRL, Neuchâtel (CH)

( * ) Notice: Subject to any disclaimer, the term of this patent is extended or adjusted under 35 U.S.C. 154(b) by 405 days.

(21) Appl. No.: 13/830,192

(22) Filed: Mar. 14, 2013

(65) Prior Publication Data
US 2014/0277210 A1    Sep. 18, 2014

(51) Int. Cl.
*A61B 17/88*    (2006.01)

(52) U.S. Cl.
CPC ......... *A61B 17/8855* (2013.01); *A61B 17/8819* (2013.01)

(58) Field of Classification Search
CPC ............... A61B 17/17; A61B 17/1728; A61B 17/1757; A61B 2017/90; A61B 19/20; A61B 19/201
USPC ............................ 606/266, 287–289, 129, 130
See application file for complete search history.

(56) References Cited

U.S. PATENT DOCUMENTS

| | | | |
|---|---|---|---|
| 4,809,694 A * | 3/1989 | Ferrara | 606/130 |
| 5,263,956 A * | 11/1993 | Nobles | 606/130 |
| 5,405,330 A | 4/1995 | Zunitch et al. | |
| 5,681,325 A | 10/1997 | Hasson | |
| 5,810,712 A | 9/1998 | Dunn | |
| 5,865,817 A | 2/1999 | Moenning et al. | |
| 5,993,463 A * | 11/1999 | Truwit | 606/130 |
| 6,039,725 A | 3/2000 | Moenning et al. | |
| 6,110,182 A | 8/2000 | Mowlai-Ashtiani | |
| 6,287,281 B1 | 9/2001 | Nishtala et al. | |
| 6,488,664 B1 | 12/2002 | Solomon et al. | |
| 8,241,341 B2 * | 8/2012 | Walker et al. | 606/306 |
| 2004/0236330 A1 * | 11/2004 | Purcell et al. | 606/61 |

* cited by examiner

*Primary Examiner* — Anu Ramana
(74) *Attorney, Agent, or Firm* — Martin & Ferraro LLP (57) ABSTRACT

A device includes a first member extending along an axis and including an inner surface defining a cavity. The inner surface defines a locking element extending into the cavity. First and second openings extend the first member and are in communication with the cavity. A pivoting member is movably disposed in the cavity and includes an inner surface defining a passageway. An outer surface of the pivoting member includes grooves configured to engage the locking element. A second member is disposed within the passageway. The pivoting member is movable between a first orientation such that the locking element is spaced apart from the grooves and the pivoting member is rotatable to a selected trajectory relative to the axis and a second orientation such that the locking element engages one of the grooves and the second member is fixed in the selected trajectory.

14 Claims, 6 Drawing Sheets

SURGICAL DEVICE WITH RATCHET MECHANISM FOR PERFORMING A SURGICAL PROCEDURE AND METHOD

TECHNICAL FIELD

The present disclosure generally relates to medical devices for the treatment of musculoskeletal structures, and more particularly to a surgical system and method that include a device configured to hold a surgical instrument while a surgical procedure is performed.

BACKGROUND

Height loss is commonly associated with fractures, such as, for example, spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing a bone void filler, such as, for example, bone cement with balloon catheter technology. The kyphoplasty procedure restores height of the collapsed spinal bone which diminishes associated back pain.

Kyphoplasty procedures may also be used to treat fractures in other areas of a patient's body, such as, for example, a distal radius of the patient. To treat a distal radius fracture using a kyphoplasty procedure, an inflatable bone tamp (IBT) is utilized. The IBT is used to percutaneously reduce comminuted, articular depressions in a controlled manner. Fracture morphologies, such as, for example, "die-punch" fractures are especially suited for correction by an IBT. IBTs are deployed to a surgical site, such as, for example, a bone defect through a working cannula. IBTs create well-defined voids. After the void is created by the IBT, the IBT is removed from the cannula and a material, such as, for example a bone void filler is delivered through the cannula and into the void. The bone void filler may be used in conjunction with percutaneous pins, ex-fixes, screws and/or plates for fracture fixation.

In conventional kyphoplasty procedures, the IBT is inserted adjacent the bone defect by inserting the IBT through a cannula. An inflatable member of the IBT is expanded to create a void in or adjacent the bone defect. After the IBT creates the void, the IBT is removed from the cannula and a bone void filler is delivered through the cannula to the void in order to at least partially fill the void. It is therefore important that the cannula be properly oriented with respect to the bone defect. In conventional kyphoplasty procedures, the cannula is held at a desired trajectory by a physician or physician's assistant, so that the IBT or bone void filler may be delivered through the cannula to a location adjacent the bone defect or void created by the IBT.

Percutaneous delivery of IBT or bone filler material through the cannula to a bone defect or bone void can be difficult. For example, the IBT or bone void filler material may get stuck in the delivery tool or cannula. Furthermore, the distal end of the cannula must be positioned adjacent to the bone defect or bone void to allow the IBT or bone void filler to be delivered through the cannula to the bone defect or bone void. In some cases there is little soft tissue and/or bony anatomy, e.g. in the distal radius, to hold the cannula in a stable position during delivery of the IBT or bone filler material. To stabilize the cannula, a surgical assistant is often required to provide an extra pair of hands to hold the cannula while a surgeon delivers the IBT or the bone filler material to the bone defect or bone void through the cannula. The present disclosure provides a device that acts as a second pair of hands to hold the cannula at a fixed trajectory to ensure that the cannula is properly positioned relative to the bone defect or bone void. This disclosure describes an improvement over these prior art technologies.

SUMMARY

Accordingly, a surgical system and method for correction of a bone injury or disorder are provided. In one embodiment, in accordance with the principles of the present disclosure, the surgical system includes a device for performing a surgical procedure. The device includes a first member extending along a longitudinal axis between a first end and a second end. The first end includes an inner surface defining a cavity. The inner surface defines a locking element extending into the cavity. The first end further includes a first opening extending through a first surface and a second opening extending through an opposite second surface. The first and second openings are in communication with the cavity. A pivoting member is movably disposed in the cavity and includes an inner surface defining a passageway. An outer surface of the pivoting member includes a plurality of spaced apart grooves configured to engage the locking element. A second member is disposed within the passageway. The pivoting member is movable between a first orientation such that the locking element is spaced apart from the grooves and the pivoting member is rotatable to a selected trajectory relative to the longitudinal axis and a second orientation such that the locking element engages one of the grooves and the second member is fixed in the selected trajectory.

In one embodiment, in accordance with the principles of the present disclosure, the system includes a device comprising a first member extending along a longitudinal axis between a first end and a second end. The first end includes an inner surface defining a substantially spherical cavity. The inner surface defines a locking element defined by a tapered projection extending parallel to the longitudinal axis from the inner surface of the first member into the cavity. The first end further includes a first opening extending through a first surface and a second opening extending through an opposite second surface. The first and second openings are in communication with the cavity. A pivoting member is movably disposed in the cavity and includes an inner surface defining a passageway. An outer surface of the pivoting member includes a plurality of spaced apart grooves configured to engage the locking element. The pivoting member including a first end comprising a ball and a second end comprising a collet. The grooves are disposed about the ball and are each tapered between a first end adjacent an outer surface of the ball and an opposite second end. At least one of the grooves extends at an acute angle relative to the longitudinal axis and at least one of the grooves extends parallel to the longitudinal axis. The grooves have an angular orientation between 1 degree and 90 degrees relative to an adjacent groove. A second member is disposed within the passageway and includes an inner surface defining a second passageway. The second passageway having an inflatable bone tamp, bone void filler or a tool configured to deliver bone void filler disposed therein. A cap has an inner surface configured to engage an outer surface of the collet. The outer surface of the collet and the inner surface of the cap are threaded. The threads on the outer surface of the collet are configured to engage the threads on the inner surface of the cap. The cap is movable between a first orientation such that the threaded inner surface of the cap is spaced apart from the threaded outer surface of the collet and the second member is movably disposed within the passageway and a second orientation such that the threaded inner surface of the cap engages the threaded outer surface of the collet and the second member is fixed within the passageway. The pivoting member is movable between a first orientation such that the locking element is spaced apart from the grooves and the pivoting member is rotatable to a selected trajectory relative to the longitudinal axis and a second orientation such that the locking element engages one of the grooves and the second member is fixed in the selected trajectory.

In one embodiment, in accordance with the principles of the present disclosure, a method for repairing a bone is provided. The method comprises the steps of: providing a device comprising: a first member extending along a longitudinal axis between a first end and a second end, the first end including an inner surface defining a cavity, the inner surface defining a locking element extending into the cavity, the first end further including a first opening extending through a first surface and a second opening extending through an opposite second surface, the first and second openings being in communication with the cavity, a pivoting member movably disposed in the cavity including an inner surface defining a passageway, an outer surface of the pivoting member including a plurality of spaced apart grooves configured to engage the locking element, and a second member disposed within the passageway; creating an access path to a defect in a bone; inserting the second end of the first member through the access path; inserting a second member into the passageway; rotating the pivoting member to a selected trajectory relative to the longitudinal axis such that a distal end of the second member is positioned adjacent the bone defect; and engaging the locking element with one of the grooves such that the second member is fixed in the selected trajectory.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method include a device configured to hold a surgical instrument while performing a surgical procedure to treat a bone defect, such as, for example a fracture.

In one embodiment, the system and method include a device configured to hold a cannula having a ball and socket configuration. The ball is configured to interface with a socket in a tail of the device. The ball includes a collet having a threaded outer surface. The ball and collet have an inner surface defining a passageway configured for disposal of a surgical tool, such as, for example, a cannula. A cap has a threaded inner surface configured to engage the threaded outer surface of the collet. As the threaded inner surface of the cap engages the threaded outer surface of the collet, the inner surface of the collet engages an outer surface of the collet to fix the cannula relative to the collet. That is, the cap tightens around the collet to rigidly hold the cannula. The socket includes at least one projection and an outer surface of the ball includes a plurality of grooves configured for disposal of the projection.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, balloons that are preformed to have different sizes and shapes.

It is envisioned that the present disclosure may be employed to treat bone disorders, such as, for example fractures in the anatomy of a patient, such as, for example, spinal bones or arm bones. It should be understood that the present principles are applicable to any bone structures, including but not limited to bones of the spine, arms, legs, feet, hands, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the arm, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system for holding a surgical instrument while a surgical procedure is performed. The disclosure also includes a description of related methods of employing the disclosed surgical system. Alternate embodiments are also disclosed. Reference will now be made in detail to the exemplary embodiments of the present disclosure, which are illustrated in the accompanying figures. Turning now to FIGS. 1-7, there are illustrated components of a surgical system, such as, for example, a surgical system 30 and embodiments in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

Figure 3:
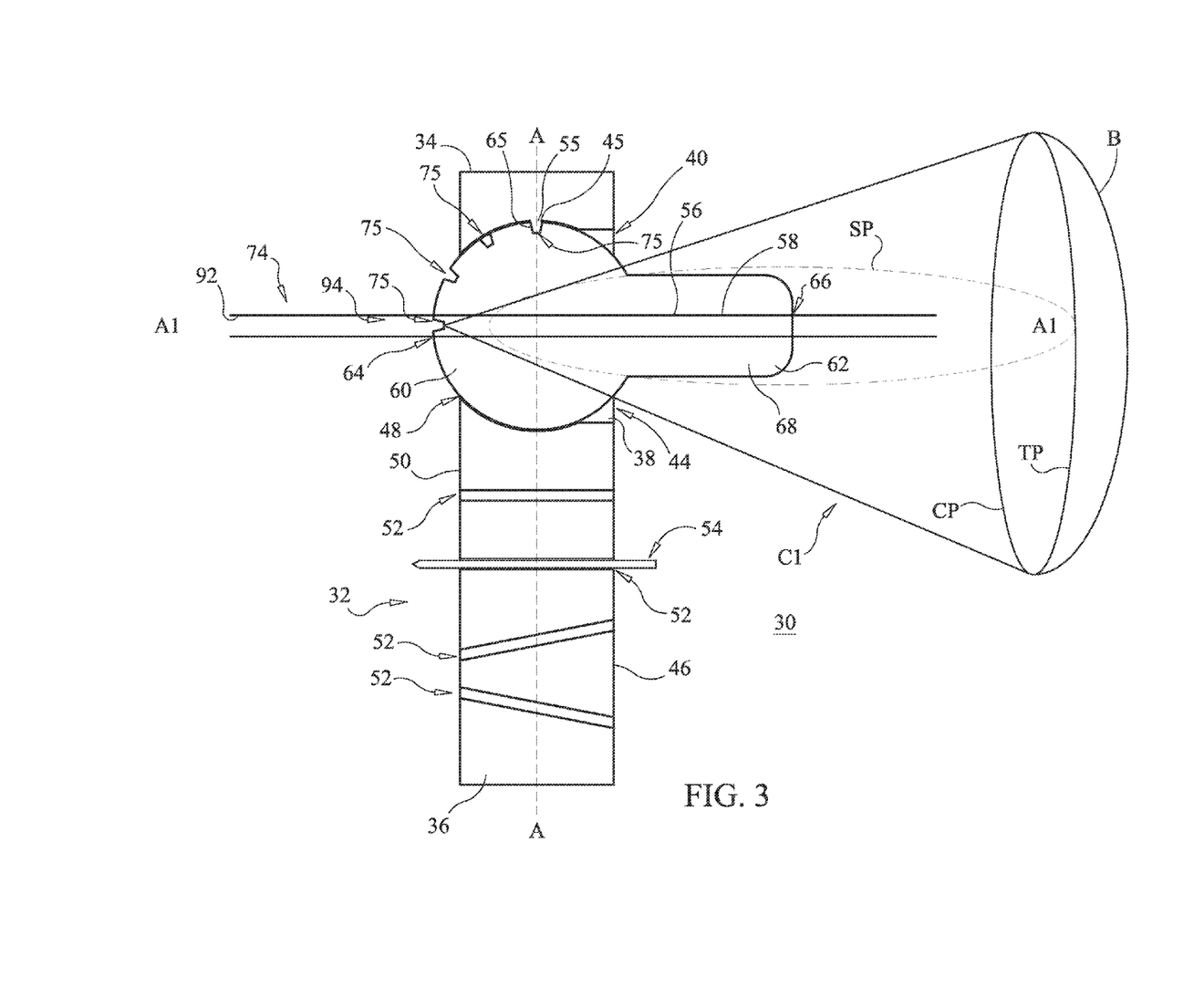
FIG. 3 is a side, cross sectional view of the system shown in FIG. 1.
Figure 4:
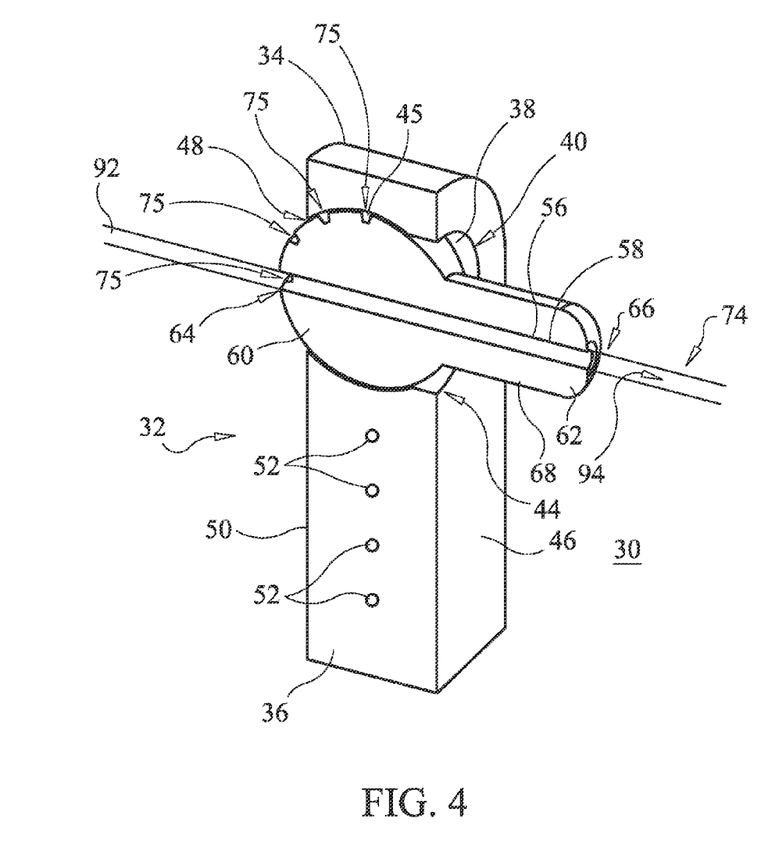
FIG. 4 is a perspective, cross sectional view of the system shown in FIG. 1.
Figure 5:
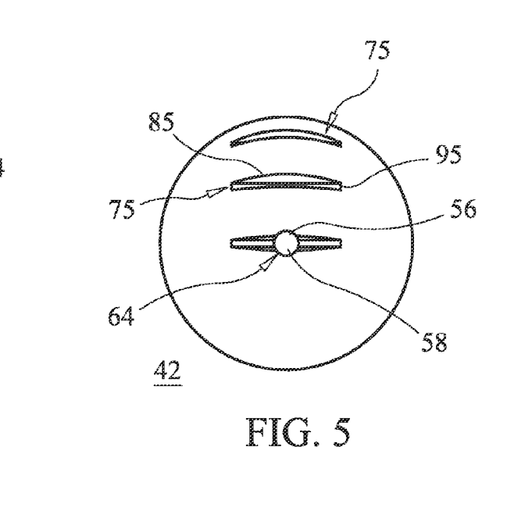
FIG. 5 is an end view of a component of the system shown in FIG. 1.

System 30 is employed, for example, with an open, mini-open or minimally invasive surgical technique to treat a bone defect, such as, for example a fracture. System 30 includes a tail, such as, for example, a first member 32 extending along a longitudinal axis A between a first end 34 and a second end 36. End 34 includes an inner surface 38 defining a substantially spherical cavity 40 extending transverse to axis A configured for movable disposal of a substantially spherical portion of a component, such as, for example, a pivoting member 42. Surface 38 defines a circular first opening 44 extending through a first surface 46 of member 32 and a circular second opening 48 extending through an opposite second surface 50 of member 32. Openings 44, 48 extend perpendicular to axis A and are in communication with cavity 40. Opening 44 has a diameter that is greater than a diameter of opening 48, as shown in FIG. 3. However, it is envisioned that this configuration may be reversed. That is, the diameter of opening 44 may be less than the diameter of opening 48. It is further envisioned that the diameter of opening 44 may be equal to the diameter of opening 48. In some embodiments, cavity 40 includes a material, such as, for example, a deformable material such as, for example, silicone or silicone rubber disposed about at least a portion of surface 38 configured to enhance engagement between an outer surface of member 42 and member 32. It is envisioned that all or only a portion of cavity 40, opening 44 and/or opening 48 may be variously configured and dimensioned, such as, for example, planar, concave, convex, arcuate, hemispherical, polygonal, irregular, uniform, non-uniform, staggered, tapered, consistent or variable, depending on the requirements of a particular application. It is further envisioned that cavity 40, opening 44 and/or opening 48 may be disposed at alternate orientations relative to axis A, such as, for example, transverse or perpendicular and/or other angular orientations such as acute or obtuse and/or may be offset or staggered and/or may be disposed at alternative angular orientations relative to axis A, depending on the requirements of a particular application.

Surface 38 includes a locking element, such as, for example, a projection 45 extending into cavity 40 in a direction that is parallel to axis A. Projection 45 includes a first portion 55 extending from surface 38 and an opposite second portion 65. Projection 45 is tapered between portions, 55, 65. In one embodiment, surface 38 includes a plurality of projections 45 that are uniformly spaced apart from one another. It is envisioned that all or only a portion of projection(s) 45 may be variously configured and dimensioned, such as, for example, planar, concave, convex, polygonal, irregular, uniform, non-uniform, staggered, tapered, consistent or variable, depending on the requirements of a particular application.

End 36 includes a cylindrical aperture 52 extending through surfaces 46, 50. Aperture 52 is configured to receive an engagement device, such as, for example a pin or K-wire 54 configured to fix member 32 relative to the anatomy of a patient. It is envisioned that end 36 may include one or a plurality of apertures 52. In some embodiments, apertures 52 are elongated slots. It is further envisioned that system 30 may include one or a plurality of pins/K-wires 54, corresponding to the number of apertures 52. In one embodiment, end 36 includes apertures 52 that all extend perpendicular to axis A. In one embodiment, end 36 includes apertures 52 extending perpendicular to axis A positioned proximally of apertures 52 extending at an acute angle relative to axis A. However, it is contemplated that this configuration may be reversed. That is, the apertures 52 that extend at an acute angle relative to axis A may be positioned proximally of the apertures 52 that extend perpendicular to axis A. It is contemplated that the apertures 52 that extend at an acute angle relative to axis A may alternate with the apertures 52 that extend perpendicular to axis A. It is envisioned that apertures 52 may be disposed through angular ranges in various orientations relative to axis A, such as, for example, transverse or perpendicular and/or other angular orientations such as acute or obtuse, and/or may be offset or staggered. In some embodiments, apertures 52 and/or pins/K-wires 54 may be rough, textured, porous, semi-porous, dimpled and/or polished to facilitate engagement between apertures 52 and pins/K-wires 54.

Member 42 includes an inner surface 56 defining a passageway 58 having a cylindrical cross sectional configuration. A first end of member 42 includes a substantially spherical ball 60 and a second end of member 42 includes a collet 62 extending from ball 60. Passageway 58 extends through ball 60 and collet 62. In one embodiment, the device does not have a collet 62 but instead passageway 58 is configured to provide a friction fit with the cannula to effectively lock the cannula in place. Member 42 includes a circular first opening 64 extending through ball 60 and a circular second opening 66 extending through collet 62. Openings 64, 66 extend perpendicular to axis A and are in communication with passageway 58. It is envisioned that all or only a portion of passageway 58, opening 64 and/or opening 66 may be variously configured and dimensioned, such as, for example, oval, oblong, triangular, square, polygonal, irregular, uniform, non-uniform, offset, staggered, undulating, planar, concave, convex, arcuate, hemispherical, polygonal, irregular, uniform, non-uniform, staggered, tapered, consistent or variable, depending on the requirements of a particular application. It is further envisioned that passageway 58, opening 64 and/or opening 66 may be disposed at alternate orientations relative to axis A, such as, for example, transverse or perpendicular and/or other angular orientations such as acute or obtuse and/or may be offset or staggered and/or may be disposed at alternative angular orientations relative to axis A, depending on the requirements of a particular application.

Figure 1:
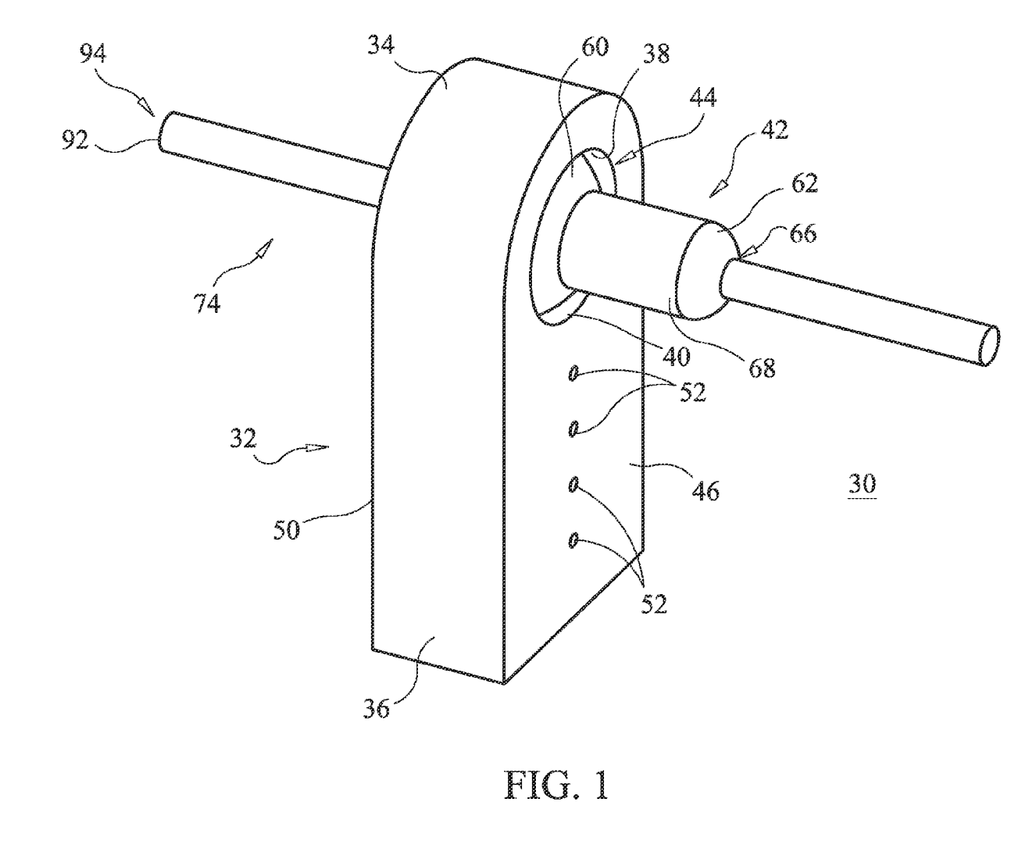
FIG. 1 is a perspective view of one embodiment of a system in accordance with the principles of the present disclosure.
Figure 2:
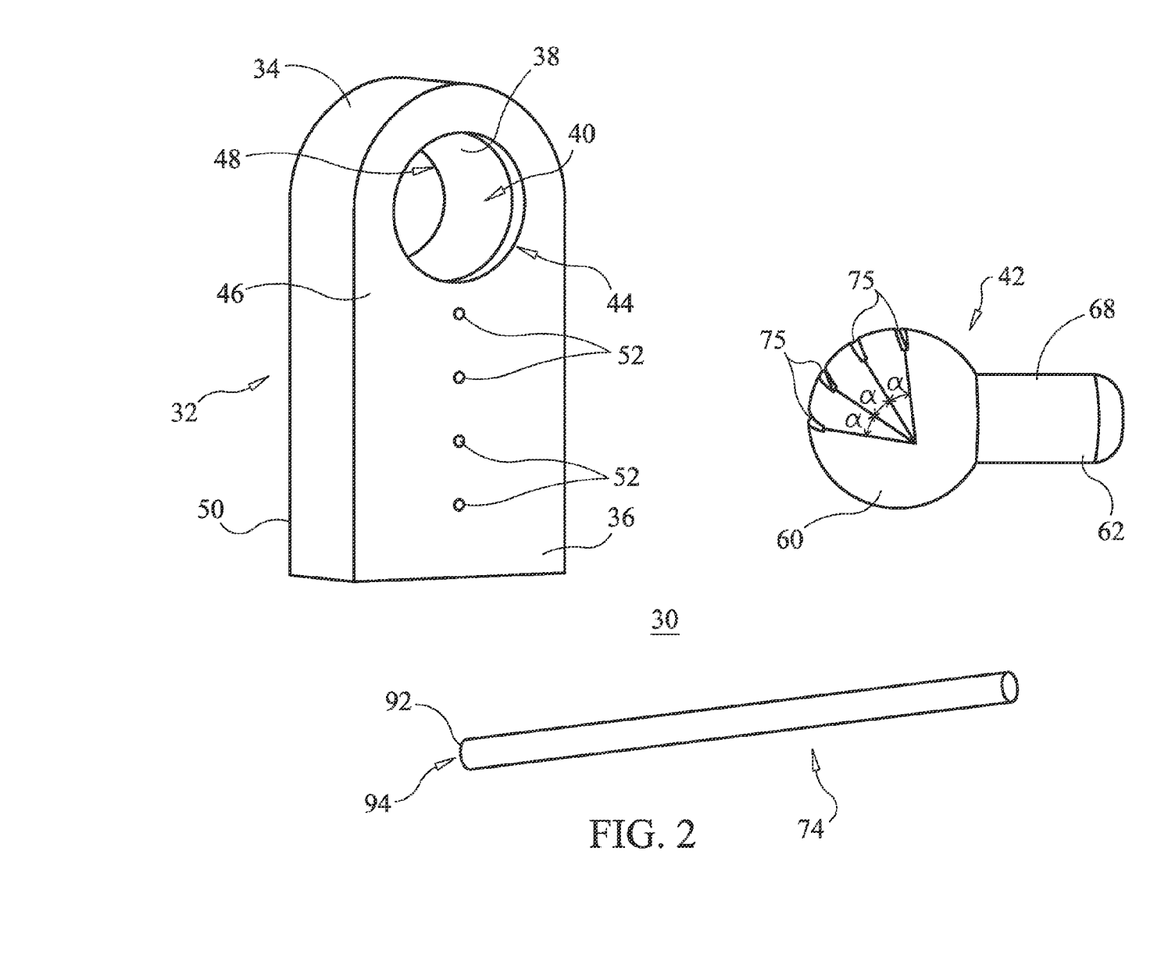
FIG. 2 is a perspective view of the system shown in FIG. 1, with parts separated.

Ball 60 includes an outer surface including a plurality of spaced apart grooves 75 each configured for disposal of projection 45 to fix member 42 relative to member 32. At least one of grooves 75 extends at an acute angle relative to axis A and at least one of grooves 75 extends parallel to axis A. In some embodiments, each of grooves 75 have an angular orientation a between 1 degree and 30 degrees relative to an adjacent groove 75. In some embodiments, each of grooves 75 have an angular orientation a that is between 1 degree and 45 degrees relative to an adjacent groove 75, as shown in FIG. 2. In some embodiments, each of grooves 75 have an angular orientation a that is between 1 degree and 20 degrees relative to an adjacent groove 75. In some embodiments, each of grooves 75 have an angular orientation a that is between 1 degree and 10 degrees relative to an adjacent groove 75. In some embodiments, each of grooves 75 have an angular orientation a that is between 1 degree and 5 degrees relative to an adjacent groove 75. In one embodiment, each of grooves 75 have an angular orientation of 22.5 degrees relative to an adjacent groove 75.

Grooves 75 are each tapered between a first end 85 adjacent the outer surface of ball 60 and an opposite second end 95. Grooves 75 are aligned by an axis defined by collet 62. However, it is contemplated that grooves 75 may be offset from the axis defined by collet. It is further contemplated that at least one of grooves 75 may be aligned with the axis defined by collet 62 and that at least one of grooves 75 may be offset from the axis defined by collet 62. It is envisioned that grooves 75 may be disposed at alternate orientations relative to axis A, such as, for example, transverse or perpendicular and/or other angular orientations such as acute or obtuse and/or may be offset or staggered and/or may be disposed at alternative angular orientations relative to axis A, depending on the requirements of a particular application. It is further envisioned that all or only a portion of each groove 75 may be variously configured and dimensioned, such as, for example, planar, concave, convex, polygonal, irregular, uniform, non-uniform, staggered, tapered, consistent or variable, depending on the requirements of a particular application.

In some embodiments, collet 62 has a substantially cylindrical configuration and includes a smooth or even outer surface 68 that is free of threads. Surface 68 is tapered toward an end of collet 62 opposite ball such that at least a portion of the end of collet 62 opposite ball 60 is rounded, as shown in FIGS. 1-4. It is envisioned that all or only a portion of collet 62 may have alternate cross section configurations, such as, for example, oval, oblong, triangular, square, polygonal, irregular, uniform, non-uniform, offset, staggered, undulating, arcuate, variable and/or tapered, depending upon the requirements of a particular application. It is further envisioned that surface 68 may have various surface configurations, such as, for example, rough, threaded for connection with other components of system 30 or surgical instruments, arcuate, undulating, porous, semi-porous, dimpled, polished and/or textured, according to the requirements of a particular application.

Figure 6:
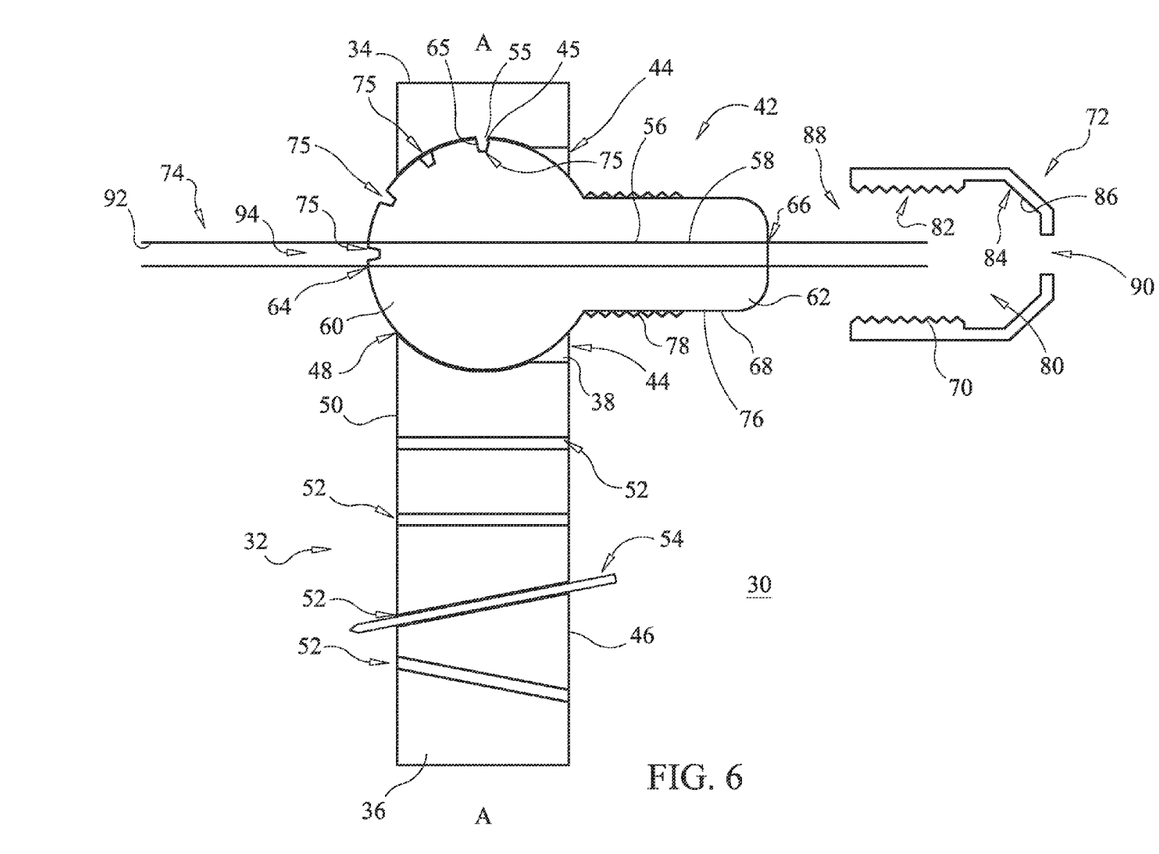
FIG. 6 is a side, cross sectional view of one embodiment of a system in accordance with the principles of the present disclosure.
Figure 7:
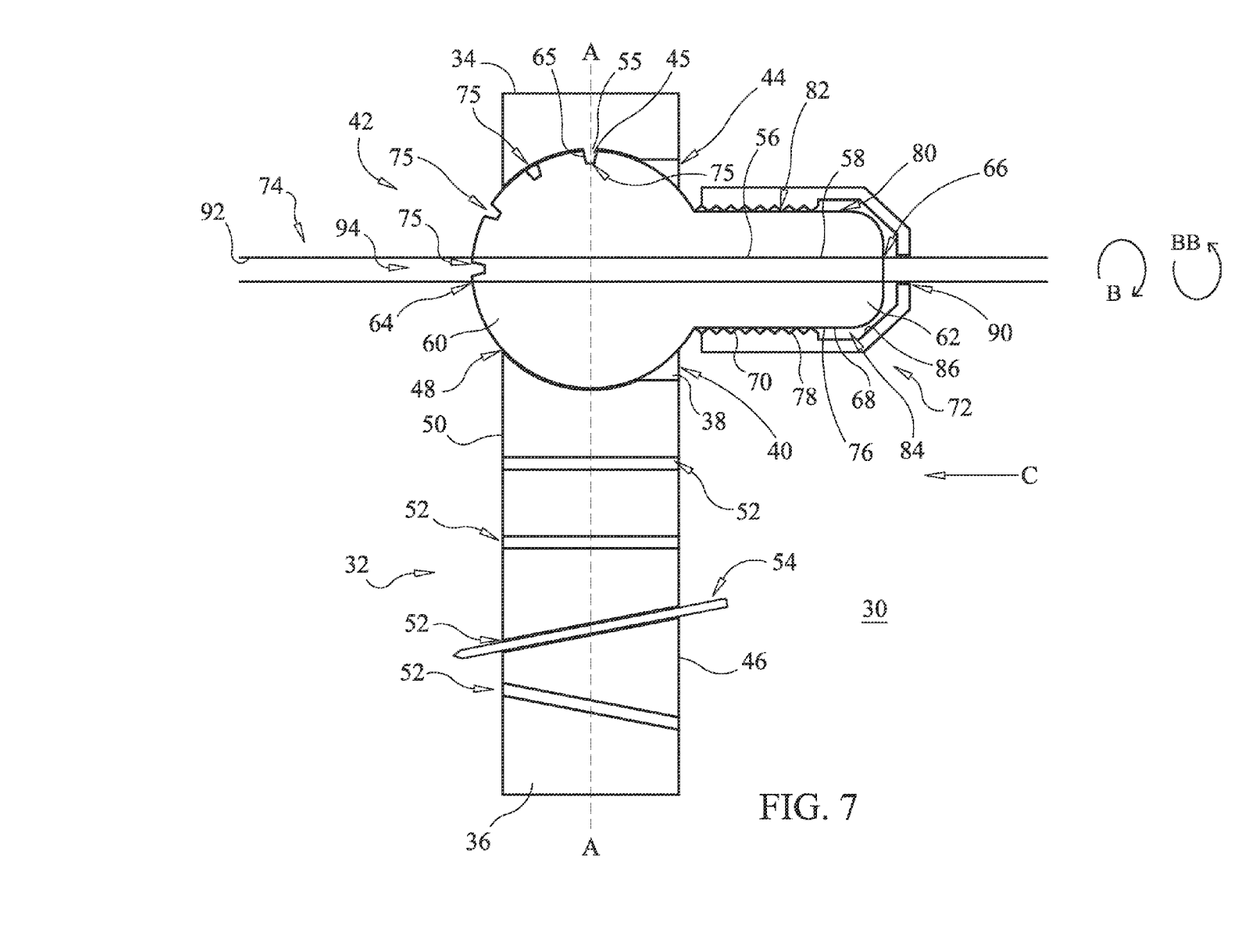
FIG. 7 is a side, cross sectional view of the system shown in FIG. 6.

In some embodiments, at least a portion of surface 68 is threaded, the threaded portion of surface 68 being configured to engage a threaded portion of an inner surface 70 of a nut, such as, for example, cap 72, as shown in FIGS. 6 and 7, to engage cap 72 with collet 62 and fix a tool, such as, for example, a cannula 74 within passageway 58. In particular, surface 68 includes an unthreaded portion 76 extending from a threaded portion 78, portion 78 extending from ball 60. It is contemplated that cap 72 may engage collet 62 to fix cannula 74 within passageway 58 in alternate fixation configurations, such as, for example, friction fit, pressure fit, locking protrusion/recess, locking keyway and/or adhesive.

Surface 70 defines a hollow interior 80 of cap 72. Surface 70 includes a threaded portion 82 at a first end of cap 72 and an unthreaded portion 84 at a second end of cap 72. Portion 84 includes an inner surface 86 extending at an acute angle relative to axis A that is free of threads. Surface 70 further defines a circular first opening 88 in the first end of cap 72 and a circular second opening 90 in the second end of cap 72.

Openings 88, 90 are in communication with interior 80. It is contemplated that opening 88 and/or opening 90 may have various cross section configurations, such as, for example, oval, oblong, triangular, rectangular, square, polygonal, irregular, uniform, non-uniform, variable and/or tapered, depending upon the requirements of a particular application. It is further contemplated that opening 88 and/or opening 90 may be disposed at alternate orientations relative to axis A, such as, for example, transverse, perpendicular and/or other angular orientations such as acute or obtuse and/or may be offset or staggered and/or may be disposed at alternative angular orientations relative to axis A, depending on the requirements of a particular application.

Portion 82 is configured to engage portion 78 to engage cap 72 with collet 62. As portion 82 engages portion 78, cap 72 is rotated in the direction shown by arrow B or arrow BB such that cap 72 translates relative to collet 62 in the direction shown by arrow C. As cap 72 translates in the direction shown by arrow C, surface 86 engages portion 76 causing collet 62 to at least partially collapse such that surface 56 engages an outer surface of cannula 74. Because surface 86 is angled, rotation of cap 72 in the direction shown by arrow B or arrow BB allows for incremental tightening of surface 56 about cannula 74 such that a restrictive force applied to cannula 74 can be adjusted by altering the amount of rotation of cap 72. When portion 82 is fully threaded with portion 78, cannula 74 becomes fixed relative to collet 62. That is, cap 72 is movable between a first orientation such that portion 82 is spaced apart from portion 78 and cannula 74 is movably disposed within passageway 58 and a second orientation such that portion 82 engages portion 78 and surface 56 engages the outer surface of cannula 74 to fix cannula 74 within passageway 58.

Cannula 74 has an inner surface 92 defining a second passageway 94 having a cylindrical cross sectional configuration adapted for disposal of an inflatable bone tamp, a bone void filler and/or a tool configured to deliver a bone void filler therein. Cannula 74 includes a circular first opening 96 extending perpendicular to axis A through a first end surface of cannula 74 and a circular second opening 98 extending perpendicular to axis A through a second end surface of cannula 74. Openings 96, 98 are in communication with passageway 94. In some embodiments, surface 92 includes a material, such as, for example, a deformable material, such as, for example, silicone or elastomer (e.g., synthetically produced butyl rubber or neoprene or a natural rubber) disposed about passageway 94 to facilitate engagement of cannula 74 with another component of system 30, such as, for example, the inflatable bone tamp or the tool configured to deliver a bone void filler. It is envisioned that all or only a portion of passageway 94, opening 96 and/or opening 98 may have alternate cross section configurations, such as, for example, circular, oval, oblong, triangular, square, rectangular, polygonal, irregular, uniform, non-uniform, offset, staggered, undulating, arcuate, variable and/or tapered, depending upon the requirements of a particular application. In one embodiment, ball 60 can a have silicone lining for friction fit with cannula 74. In another embodiment, ball 60 can snap onto cannula 74 instead of sliding through a hole.

Member 42 is movable between a first orientation such that projection 45 is spaced apart from grooves 75 and member 42 is rotatable to a selected trajectory relative to axis A and a second orientation such that projection 45 is disposed in at least one of grooves to fix member 42 in the selected trajectory. When member 42 is in the first orientation, passageway 58 is rotatable to a selected angle through and within angular range α relative to axis a in a plurality of planes that lie in a cone configuration C1, as shown in FIG. 3. The area and/or volume defined by cone C1, which includes the configuration disposed between a transverse axis A1 and a circular base B, is defined by the range of motion of passageway 58 axis A1. The plurality of planes includes a locus of all straight line segments that join axis A1 and base B. For example, passageway 58 is separately rotatable to a selected angle within angular range β in each plane corresponding to a particular straight line segment that lies in cone configuration C1. It is contemplated that passageway 58 may rotatable through the individual diameters, chords, section and/or radii of base B and/or other portions of cone C1. In one embodiment, passageway 58 is rotatable to a selected angle within angular range β in a transverse plane (TP), corresponding to a particular plane that lies in cone C1. In one embodiment, passageway 58 is rotatable to a selected angle within angular range β in a coronal plane (CP), corresponding to a particular plane that lies in cone C1. It is envisioned that system 30 may be adapted such that passageway 58 is also rotatable to a selected angle within angular range β in a sagittal plane (SP), corresponding to a particular plane that lies in cone C1.

In assembly, operation and use, system 30 is employed with a surgical procedure, such as, for a correction or treatment of a bone defect, such as, for example, a fracture. It is contemplated that one or all of the components of system 30 can be delivered or implanted as a pre-assembled device or can be assembled in situ. System 30 may be completely or partially revised, removed or replaced. For example, system 30 can be employed with a surgical correction treatment of an applicable condition or injury of an affected portion of a patient, such as, for example, a distal radius or a vertebra. It is envisioned that system 30 may also be used to treat other affected portions of the patient, such as, for example, a calcaneus bone, bones of the feet or hands, bones of the legs, etc.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 30 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 30 is determined according to the configuration, dimension and location of a selected section of the bone fracture and the requirements of a particular application.

An incision is made in the body of a patient and a cutting instrument (not shown) creates a surgical pathway for implantation of components of system 30. This may include the use of a cannula or other device. A preparation instrument (not shown) can be employed to prepare tissue surfaces, as well as for aspiration and irrigation of a surgical region according to the requirements of a particular surgical application.

Portion 82 is aligned with portion 78. Cap 72 is rotated in the direction shown by arrow B or arrow BB such that portion 82 engages portion 78 and cap 72 translates relative to collet 62 in the direction shown by arrow C. Cap 72 is translated in the direction shown by arrow C until surface 86 engages portion 76 causing inner surface 56 to engage the outer surface of cannula 74 such that cannula 74 is fixed relative to member 42. Member 42 is then rotatable to a selected trajectory relative to axis A such that cannula 74 is positioned adjacent the bone disorder. Member 42 is rotated relative to member 32 such that projection 45 is disposed in one of grooves 75 to fix member 42 in the selected trajectory.

Pins/K-wires 54 are positioned within through apertures 52 and are disposed in the anatomy of the patient, such as, for example, tissue, to fix or stabilize member 32 relative to the anatomy of the patient, with cannula 74 positioned within passageway 58. Member 32 is stabilized with pins/K-wires 54.

An inflatable bone tamp may then be delivered through cannula 74 to a location adjacent the bone disorder or defect. The inflatable bone tamp may then be expanded to create a cavity or void in the bone by delivering a material, such as, for example, saline, a contrast solution or compressed air into an expandable member of the inflatable bone tamp, such as, for example, a balloon, to move the balloon from an unexpanded configuration to an expanded configuration. As the balloon moves from the unexpanded configuration to the expanded configuration, the balloon creates a void in the bone having the defect or disorder. Member 42 maintains cannula 74 in a stabilized orientation with respect to the body such that a single practitioner can insert the inflatable bone tamp through cannula 74 and operate the inflatable bone tamp in a steady manner. That is, cannula 74 remains at the selected trajectory such that a distal end of cannula 74 is positioned adjacent the bone defect, without the need for a physician or physician's assistant to hold cannula 74.

After the void is formed in the bone, the inflatable bone tamp is removed from cannula 74. Bone filler material or a separate tool configured to deliver bone filler material is then positioned in cannula 74 so as deliver the bone filler material into the void so as to at least partially fill the void and realign fragments of the fracture and/or elevate collapsed bone to its proper height. Member 42 maintains cannula 74 in a stabilized orientation with respect to the body such that a single practitioner can administer the bone filler material in a steady manner. That is, cannula 74 remains at the selected trajectory such that a distal end of cannula 74 is positioned adjacent the bone defect, without the need for a physician or physician's assistant to hold cannula 74. It is envisioned that the bone filler material may include autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables.

The components of system 30 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these embodiments, which, nevertheless, fall within the spirit of the present disclosure, whose scope is defined by the claims set forth below.

What is claimed is:

1. A device for holding a surgical tool comprising:
a first member extending along a longitudinal axis between a first end and a second end, the first end including an inner surface, the inner surface defining a cavity, the first member further including a first surface, an opposite second surface, a first opening extending through the first surface, and a second opening extending through the opposite second surface, the first and second openings being in communication with the cavity;
at least one locking element defined on the inner surface, the at least one locking element extending from the inner surface into the cavity;
a pivoting member movably disposed in the cavity, the pivoting member defining a first passageway, the first passageway defining a transverse axis, the transverse axis being transverse to the longitudinal axis, an outer surface of the pivoting member including a plurality of spaced apart grooves, at least one groove of the plurality of spaced apart grooves being configured to engage the at least one locking element; and
a second member disposed within the passageway,
wherein the pivoting member is movable between a first orientation such that the at least one locking element is spaced apart from the at least one groove and the pivoting member is rotatable to a selected trajectory of a plurality of discrete trajectories relative to the longitudinal axis, and a second orientation such that the at least one locking element engages the at least one groove and the second member is fixed in the selected trajectory;
wherein when the pivoting member is in the first orientation, the pivoting member is rotatable along the plurality of discrete trajectories, each trajectory defining a selected angle through and within an angular range relative to the transverse axis in a plurality of planes, the plurality of planes defining a cone.

2. A device according to claim 1, wherein the locking element is a projection extending from the inner surface into the cavity.

3. A device according to claim 2, wherein the projection extends parallel to the longitudinal axis from the inner surface into the cavity.

4. A device according to claim 1, wherein the at least one locking element is a projection including a first portion extending from a first portion of the inner surface and an opposite second portion extending from a second portion of the inner surface, the first and second portions defining a tapered projection.

5. A device according to claim 1, wherein the cavity is spherical.

6. A device according to claim 1, wherein a deformable material is disposed about at least a portion of the cavity, the deformable material being configured to maintain the pivoting member in the second orientation.

7. A device according to claim 1, wherein the pivoting member includes a first end comprising a ball and a second end comprising a collet, the plurality of spaced-apart grooves being disposed about the ball, along the transverse axis.

8. A device according to claim 7, wherein at least a first groove of the plurality of grooves extends at an acute angle relative to the longitudinal axis and at least a second groove of the plurality of grooves extends parallel to the longitudinal axis.

9. A device according to claim 7, wherein at least a first groove of the plurality of grooves is tapered between a first end adjacent an outer surface of the ball and an opposite second end.

10. A device according to claim 7, wherein each groove of the plurality of grooves has an angular orientation between 1 degree and 30 degrees relative to an adjacent groove of the plurality of grooves.

11. A device according to claim 7, wherein each groove of the plurality of grooves has an angular orientation that is 22.5 degrees relative to an adjacent groove of the plurality of grooves.

12. A device according to claim 1, wherein the second member includes an inner surface defining a second passageway, the second passageway having an inflatable bone tamp disposed therein.

13. A device according to claim 1, wherein the second member includes an inner surface defining a second passageway, the second passageway having a bone void filler or a tool configured to deliver a bone void filler disposed therein.

14. A device according to claim 1, wherein the cone includes a circular base, and the plurality of planes include a locus of straight line segments that join the transverse axis to the circular base.

* * * * *